United States Patent [19]
Redmon

[11] Patent Number: 5,569,300
[45] Date of Patent: Oct. 29, 1996

[54] DILATING SURGICAL FORCEPS HAVING ILLUMINATION MEANS ON BLADE INNER SURFACE

[76] Inventor: Henry A. Redmon, 12029 Orange Grove Dr., Tampa, Fla. 33618

[21] Appl. No.: 420,812

[22] Filed: Apr. 12, 1995

[51] Int. Cl.⁶ .............................. A61B 1/313; A61B 17/28
[52] U.S. Cl. ........................... 606/207; 606/191; 600/219; 600/223; 600/245; 604/104
[58] Field of Search ..................................... 600/212, 215, 600/217–19, 223, 225, 245; 604/104; 606/191, 205, 207; 128/200.26

[56] References Cited

U.S. PATENT DOCUMENTS

| | | |
|---|---|---|
| 614,854 | 11/1898 | Frank et al. . |
| 1,097,978 | 6/1913 | Johnson . |
| 3,664,330 | 9/1969 | Deutsch .................................. 600/219 |
| 3,762,400 | 10/1973 | McDonald .............................. 600/212 |
| 3,893,454 | 7/1975 | Hagelin . |
| 4,502,485 | 3/1985 | Burgin .................................... 600/219 |
| 4,889,112 | 12/1989 | Schachner et al. . |
| 5,014,407 | 5/1991 | Boughten et al. . |
| 5,089,000 | 2/1992 | Agee et al. ............................. 606/170 |
| 5,217,007 | 6/1993 | Ciaglia . |
| 5,217,460 | 6/1993 | Knoepfler ............................... 606/207 |
| 5,454,365 | 10/1995 | Bonutti ................................... 600/204 |

FOREIGN PATENT DOCUMENTS

| | | | |
|---|---|---|---|
| 1091700 | 10/1960 | Germany | ............................... 606/207 |

*Primary Examiner*—Richard J. Apley
*Assistant Examiner*—Kelly McGlashen
*Attorney, Agent, or Firm*—Diller, Ramik & Wight, PC

[57] ABSTRACT

A surgical instrument is provided for performing surgery to relieve the symptoms of carpal tunnel syndrome. The surgical instrument includes a pair of pivotally connected legs with each leg including a handle portion and a blade portion with the blade portions terminating in a nose. The nose is inserted through an incision in the wrist area and progressively "worked" into an area between the transverse carpal ligament. The surgical instrument is rotated approximately 90 degrees and the handle portions are then squeezed to spread the blade portions to create a surgical area fully exposing the transverse carpal ligament. One of the blade portions carries illuminating means for illuminating the surgical area or arena to assure that only the transverse carpal ligament is severed to prevent damage to the median nerve, tendons and the like passing through the carpal tunnel. Upon the severance of the transverse carpal ligament, the surgical instrument is reversed relative to the movements just described for effecting the withdrawal thereof and the incision is subsequently sutured.

12 Claims, 3 Drawing Sheets

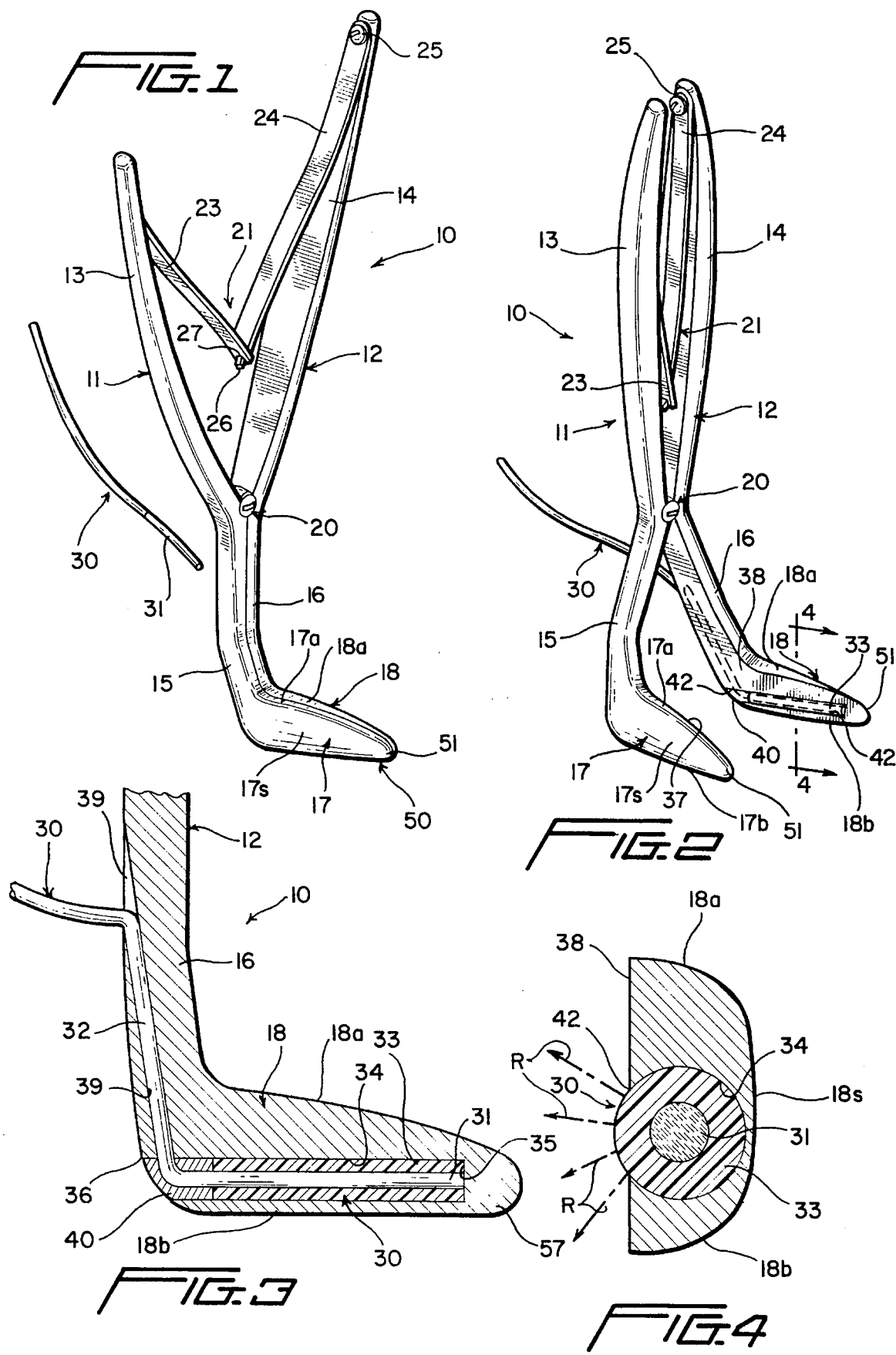

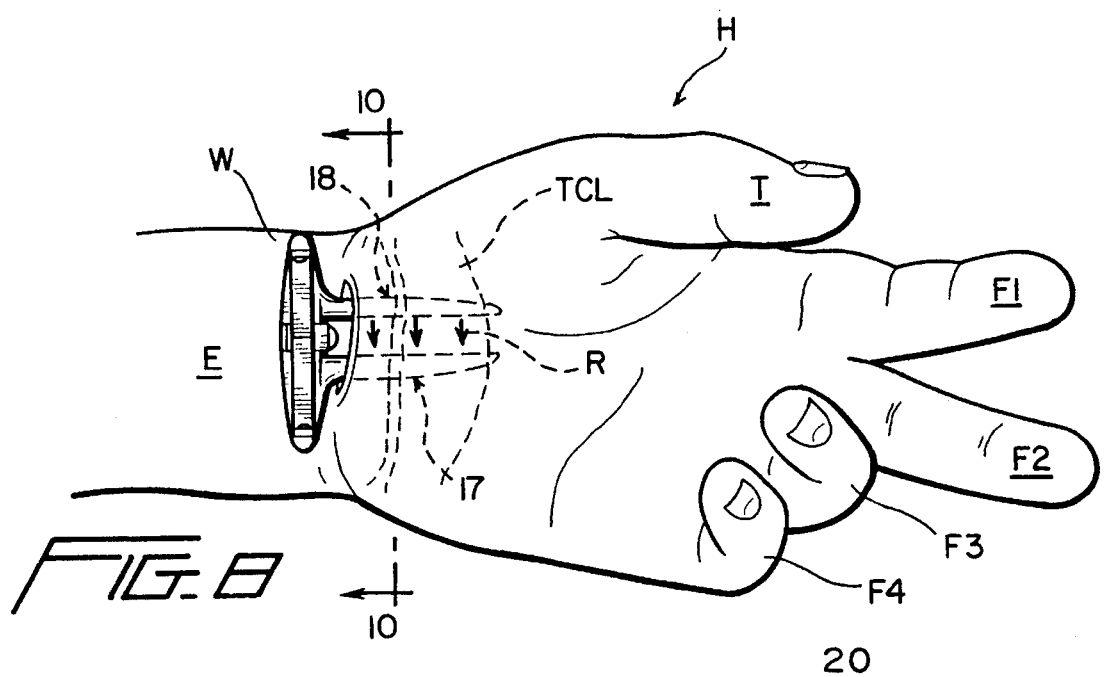
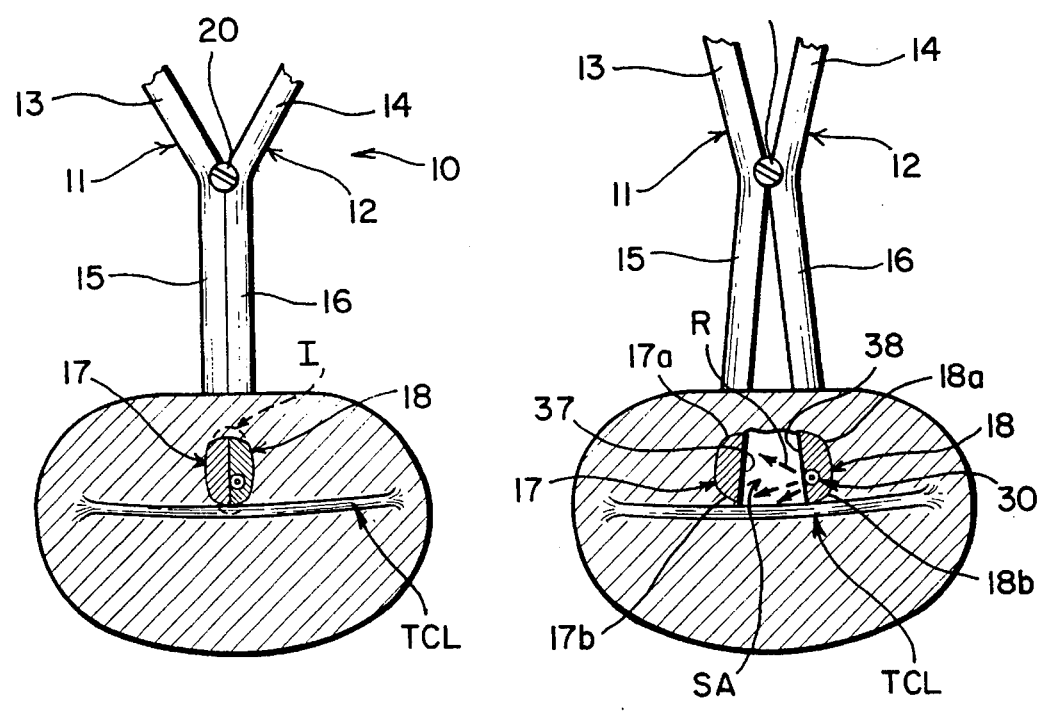

DILATING SURGICAL FORCEPS HAVING ILLUMINATION MEANS ON BLADE INNER SURFACE

BACKGROUND OF THE INVENTION

The invention relates to a surgical instrument for and a method of performing subcutaneous surgery, specifically the utilization of the surgical instrument to illuminate the carpal tunnel area of a patient to effect the severance of the transverse carpal ligament.

The carpal tunnel is a small channel formed by the carpal bones of the wrist. The median nerve runs through it and provides sensation and feeling to much of a person's hand. Tendons that connect to the fingers also run through the carpal tunnel. The median nerve and those tendons stretch and retract and press the top of the carpal tunnel during repetitive hand motions, and long term stress irritates the tendons causing the same to swell. As the tendons swell even more they press against the median nerve causing irritation, irritation feeds upon itself, cycle after cycle, and thus is the beginning of carpal tunnel syndrome.

The first warning symptoms of carpal tunnel syndrome generally are slight tingling in one's fingertips which can continue accompanied by increasing pain until pain reaches an excruciating level. Hand function is also severely impaired.

At times the only relief afforded a person afflicted with carpal tunnel syndrome is through surgery, and heretofore there were two distinct surgical approaches. In one case a relatively large incision is made to gain access to the surgical area, but obviously this is undesirable because a relatively large incision involves increased pain, longer mend time, a larger scar, etc. The alternative is endoscopic surgery which obviates the latter problems but reduces visibility and can create a far greater problem should the lack of visibility result in the inadvertent or accidental cutting of the median nerve. The latter conventional surgical methods and disadvantages related thereto have led to the development of the present surgical instrument and the surgery associated therewith involving a very minor incision followed by the utilization of the surgical instrument to both enlarge and illuminate the carpal tunnel surgery arena and assure severance of only the transverse carpal ligament absent damage to the median nerve and/or muscles, tendons, ligaments passing through the carpal tunnel.

Various instruments are provided for a variety of surgical procedures, and during a prior art search of the present invention, several patents worthy of comment were uncovered and include the following:

U.S. Pat. No. 3,893,454 in the name of Karl W. Hagelin issued on Jul. 8, 1975 discloses a coniotomy instrument which includes a speculum portion defined by two separable specula blades each carried by a leg with the legs being pivotally secured relative to each other. A spring biases a handle portion of the legs away from each other and by squeezing the handle portions the specula blades can be spread. A knife unit is carried by the specula blades and has a point which projects beyond the ends of the specula blades. The knife penetrates soft portions of the throat and into the lumen of the trachea under thumb pressure creating an incision which is widened by spreading the specula blades.

U.S. Pat. No. 614,854 issued on Nov. 29, 1898 to A. Frank et al. discloses an intubator defined by a pair of pivotally united levers having at one end a handle and at the other end a pair of jaws which are relatively slender, somewhat conical, and are designed for insertion within the interior of intubation tubes.

U.S. Pat. No. 1,097,978 in the name of C. L. Johnson issued on May 26, 1914 discloses a dilator and catheter instrument formed by a pair of members pivotally connected together having handles at one end and jaws at an opposite end which can be spread against the bias of a spring.

U.S. Pat. No. 889,112 granted to A. Schachner et al. on Dec. 26, 1989 discloses an instrument for performing a tracheostomy operation including a pair of pivotal members having hand grips at one end and an elongated nose at the opposite end thereof. The elongated noses are substantially of a conical configuration decreasing in diameter toward outer tips for facilitating the insertion of the noses into a trachea opening. The two elongated noses are movable apart by squeezing the handle grips toward each other to widen the trachea opening and thereby to facilitate the insertion of a cannula therethrough.

U.S. Pat. No. 5,014,409 in the name of L. Boughten et al. granted on May 14, 1991 illustrates a tool defined by a pair of pivotally connected lever arms having handles at one end and tips at opposite ends for gripping and/or expanding items.

U.S. Pat. No. 5,217,007 granted to P. Ciaglia on Jun. 8, 1993 discloses a speculum for forming an ostomy in a trachea. The speculum includes a pair of opposing, pivotally interconnected elongated members and respective distal nose portions extending distally from the elongated members. The elongated members have respective handle portions of which the distal nose portions extend laterally therefrom. The handles are squeezed against the bias of springs to spread the distal nose portions.

SUMMARY OF THE INVENTION

In its broadest aspects the surgical instrument of the present invention is utilized in conjunction with surgery to relieve carpal tunnel syndrome by cutting the transverse carpal ligament. The surgical instrument includes a pair of legs pivotally connected to each other and having a blade portion at one end and a handle portion at an opposite end. The blade portions define a nose which can be inserted into a relatively small incision adjacent the area of the carpal tunnel after which the instrument is rotated approximately 90° and the handle portions pressed to spread the blade portions to enlarge the carpal tunnel surgical arena. One of the blade portions includes an illuminating means, preferably in the form of fiberoptics for illuminating the area between blade portions which assures optimum visibility for effecting the severance of the transverse carpal ligament absent damage to adjacent anatomical structure, such as the median nerve and associated ligaments and tendons passing through the carpal tunnel. By directing the light rays generally normal to the blade portion carrying the fiberoptics, the surgical area is highly illuminated to thus provide both high visibility and high accessibility to the surgical area, as compared to the absence thereof in known prior art surgical procedures.

Pursuant to the method of this invention, a small incision of a determinate length is made in a patient's skin and a nose formed by closed blade portions of the instrument is progressively inserted through the incision with a relatively broad width defining surface of one of the blade portions being contiguous the epidermis adjacent the incision. Once the blade portions are inserted through the incision into the carpal tunnel area, and specifically palmar the transverse carpal ligament, the surgical instrument is rotated substantially 90° about the longitudinal axis of the blade which brings a relatively narrow thickness defining surface of the blade portions contiguous the epidermis. The latter rotational movement basically transforms the horizontal closed nature of the incision to a vertical elongated opening which is subsequently spread further along the entirety of the blade portions by moving the same away from each other to create a volume beneath the epidermis accessible through the incision opening for the eventual severance of the transverse carpal ligament. Upon completion of the latter procedure, the surgical instrument is closed and rotated to its initial insertion position, withdrawn from the incision and the incision is subsequently closed by suturing or the equivalent.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a perspective view of a novel surgical instrument constructed in accordance with this invention and illustrates a pair of legs pivotally connected by an associated pivot with each leg being defined by a handle portion and a blade portion, and further illustrated is illuminating means prior to being associated with the surgical instrument in the form of a fiberoptic endo-illuminator.

FIG. 2 is a perspective view of the surgical instrument of FIG. 1 and illustrates the blade portions thereof pivoted away from each other exposing the fiberoptic endo-illuminator carried by one of the blade portions.

FIG. 3 is an enlarged vertical cross sectional view through a portion of the leg and blade portion carrying the fiberoptic endo-illuminator, and illustrates details thereof.

FIG. 4 is an enlarged cross sectional view taken generally along line 4—4 of FIG. 2, and illustrates a generally cylindrical chamber within which is retained an end of the fiberoptic endo-illuminator in a manner which projects light rays therefrom generally transversely of an associated end face of the blade portion.

FIG. 8 is another diagrammatic top plan view similar to FIGS. 5–7, and illustrates the blade portions spread by squeezing the handle portions relative to each other, as shown in FIG. 2, to enlarge the surgical arena to access the transverse carpal ligament from above.

FIG. 9 is an enlarged cross sectional view taken generally along line 9—9 of FIG. 7, and illustrates the position of the nose portions of the surgical instrument after having been rotated from the position shown in FIG. 6 to the position shown in FIG. 7.

FIG. 10 is an enlarged cross sectional view taken generally along line 10—10 of FIG. 8, and illustrates the enlargement of the surgical arena and the manner in which the same is illuminated by the fiberoptic endo-illuminator.

DESCRIPTION OF THE PREFERRED EMBODIMENT

Figure 5:
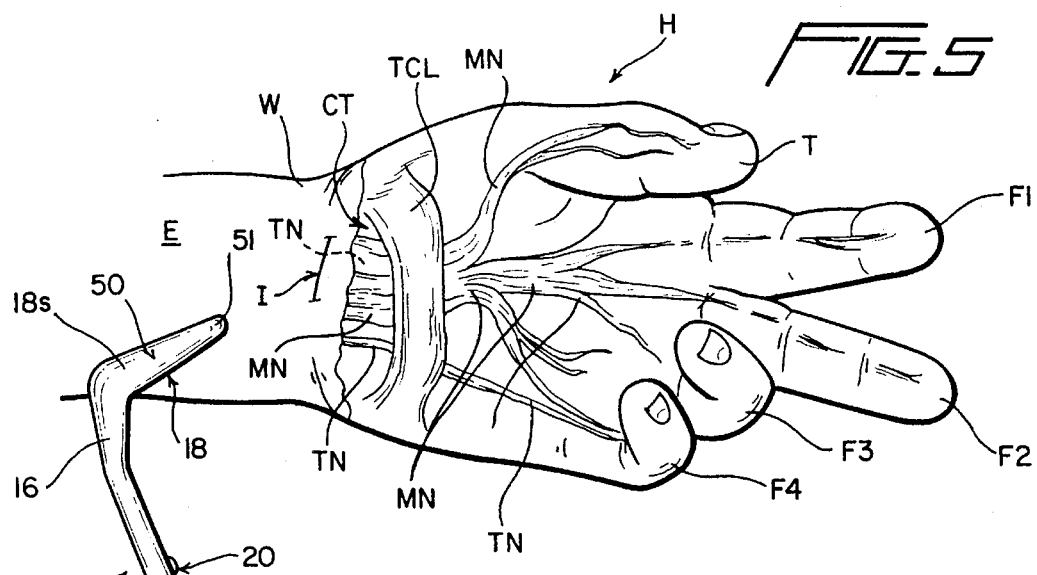
FIG. 5 is top plan view palm side up of a left hand, and illustrates the carpal tunnel; muscles, tendons and the median nerve passing therethrough, a relatively small incision adjacent the carpal tunnel, and the orientation of the surgical instrument prior to being moved through the incision into the carpal tunnel area.

A novel surgical instrument constructed in accordance with this invention designed particularly for performing carpal tunnel surgery is generally designated by the reference numeral 10 (FIGS. 1 and 2).

The surgical instrument 10 includes a pair of legs 11, 12 each constructed from surgical steel or the like, and each including a respective handle portion 13, 14, a neck portion, 15, 16 and a blade portion 17, 18. Means generally designated by the reference numeral 20 is provided for pivotally uniting or interconnecting the legs 11, 12 generally between the handle portions 13, 14 and the neck portions 15, 16, respectively. The pivoting means 20 is a conventional pivot pin or screw which permits the legs 11, 12 to be pivoted between the positions shown in FIGS. 1 and 2 of the drawings.

Spring means 21 is defined by a pair of individual springs 23, 24, connected to the leg portions 13, 14, respectively, by a threaded screw 25 or the equivalent thereof. The spring 24 has a projecting nose 26 which is received in an aperture 27 of the spring 23. The spring means or spring 21 normally biases the handle portions 13, 14 away from each other and similarly biases the blade portions, 17, 18 toward each other, as shown in FIG. 1, although the handle portions 13, 14 can be squeezed toward each other (FIG. 2) against the bias of the spring 21 to spread the blade portions 17, 18 for a purpose which will be described more fully hereinafter.

Means 30 is provided for illuminating an area between the blade portions 17, 18, particularly between respective relatively flat blade portion faces, 37, 38 thereof when the blade portions 17, 18 are pivoted or spread apart, as shown in FIGS. 2 and 10. The illuminating means 30 is a conventional fiberoptic endo-illuminator, such as Model MBS1010 distributed by Storz Ophthalmics Inc. of 3365 Tree Court Industrial Blvd., St. Louis, Mo., USA 63122-6694. The fiberoptic endo-illuminator 30 includes a light ray emitter end 31 of a flexible light conductor 32 housed within a transparent annular sheath 33 which is fixed in a cylindrical bore 34 drilled in the blade portion 18. The bore 34 has a blind end defined by a cylindrical wall 35 and a circular opening 36 opposite thereto. A narrower bore 39 is formed in the neck 16 and merges with the bore 34. In order to assemble the flexible light conductor 32 relative to the transparent annular sheath 33, the transparent annular sheath 33 is inserted into the cylindrical bore 34 through the opening 36 thereof until it abutts the blind end 35. The flexible light conductor 32 is threaded downwardly into the bore 39 and the end thereof eventually exits the bore 39 and enters the bore 34 adjacent the opening 36. The terminal end (unnumbered) of the light ray emitter end 31 is then slid into the transparent annular sheath 33 until it contacts the blind end 35 of the bore 34, as shown in FIG. 3. At this point inert liquid bonding material 40, which is preferably opaque, is poured or injected into the portion of the cylindrical bore 34 adjacent the opening 36 thereof. The bonding material 40, which can be any of today's super-glue type adhesives, will bond to glass, glass fibers and metal. Light from a suitable light source when energized, will be conducted through the flexible light conductor 32 which is essentially a group of light-conducting glass filaments, will be emitted through the light ray emitting end 31 and the transparent annular sheath 33 as light rays R which are emitted along the entire length of the sheath 33 as light rays R generally transverse to the blade portion flat face 38, as is best seen in FIG. 4. Essentially the light rays R exit through an elongated slot 42 defined by upper and lower edges (unnumbered) of the cylindrical bore 34 which opens through the blade portion flat face 38. It should also be noted that since the vertical height of the slot 42, as viewed in FIG. 4, is less than the diameter of the annular sheath 33, the upper and lower edges (unnumbered) of the elongated slot 42 retain the transparent annular sheath 33 within the cylindrical bore 34.

The blade portions 17, 18 collectively define a nose 50 (FIG. 1) when the blade portions 17, 18 are closed (FIG. 1) with the nose 50 terminating at a nose terminal end portion 51. The nose 50 generally tapers from a maximum size cross section adjacent the necks 15, 16 to its smallest cross section at the nose terminal end portion 51. The particular cross sectional configuration of each of the blade portions 17, 18 is set off or defined by respective upper surfaces 17u, 18u; relatively broad side surfaces 17s, 18s, and relatively narrow lower or bottom surfaces 17b, 18b.

SURGICAL METHOD

Figure 6:
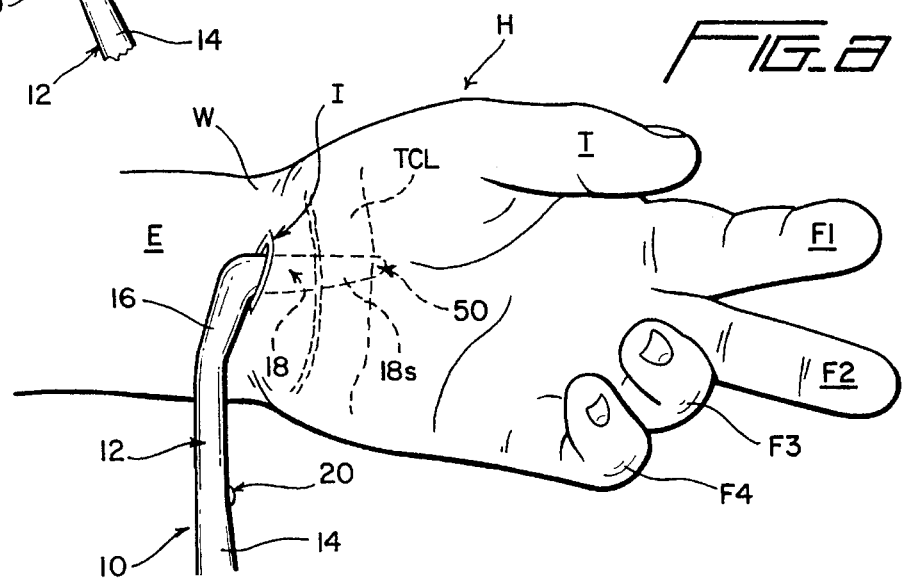
FIG. 6 is top plan diagrammatic similar to FIG. 5, and illustrates the blade portions fully inserted into the carpal tunnel area above the transverse carpal ligament.
Figure 7:
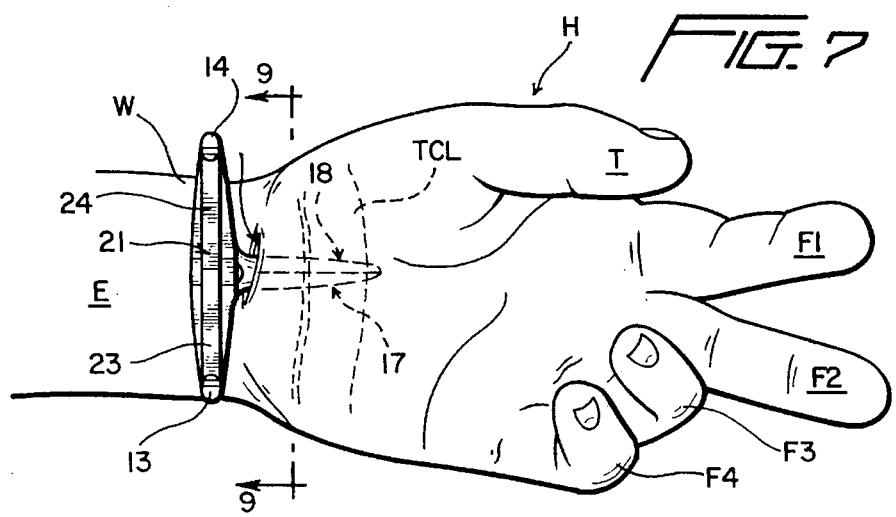
FIG. 7 is a diagrammatic top plan view similar to FIGS. 5 and 6, and illustrates the surgical instrument rotated approximately 90° from the position shown in FIG. 6.

Reference is now made to FIG. 5 of the drawings in which a left-hand illustrated palm-up is generally designated by the reference numeral H which includes a wrist W, a thumb T and a plurality of fingers F1–F4. The carpal tunnel CT is a small channel formed in part by carpal bones (not shown) of the wrist W which is bridged by the transverse carpal ligament TCL. The median nerve MN runs through the carpal tunnel CT and provides sensation and feeling to the thumb T and fingers F1–F4 of the hand H. A number of tendons TN that connect to the fingers also pass through the carpal tunnel CT. The median nerve MN and the various tendons TN stretch and contract as the hand M and wrist W are manipulated, and they also press the top of the carpal tunnel CT and the transverse carpal ligament TCL which over long term repeated stress irritates the tendons TN causing swelling which in turn results in the tendons TN pressing against the median nerve MN which cycle after cycle, results in carpal tunnel syndrome. Carpal tunnel syndrome is alleviated, however, by severing the transverse carpal ligament TCL and to the latter end a small incision I (FIG. 5) of a determinate length is made in and through the epidermis E. The nose 50 of the surgical instrument 10 is then positioned with either relatively broad width defining surface 17s or 18s of the respective blade portions 17 and 18 against or closely proximate the skin of the wrist W, generally as shown in FIG. 5, which illustrates the surface 17s of the blade portion 17 against the wrist W. The nose terminal end portion 51 is then inserted into the incision I and progressively worked into the area of the carpal tunnel CT until the nose 50, including the blade portions 17, 18 thereof, is immediately adjacent and above or palmar to the transverse carpal ligament TCL, as shown in FIGS. 6 and 9. Thereafter, while the blade portions 17, 18 are still closed, the surgical instrument 10 is rotated approximately 90° about the longitudinal axis of the blade 17 from the position shown in FIG. 6 to the position shown in FIG. 7 which increases the vertical height of the incision I and the volume (unnumbered) created by the nose 50 which will subsequently form a surgical area SA (FIG. 10) which exposes and through which can be viewed from above the transverse carpal ligament TCL. The surgical area SA is created by squeezing the handle portions 13, 14 toward each other, to the position generally shown in FIG. 2, which causes the blade portions 17, 18 to move away from each other during pivoting about the pivot pin 20. At this point the transverse carpal ligament TCL spans or bridges the lower or bottom surfaces 17b, 18b of the respective blade portions 17, 18 and is readily observable and distinguishable, particularly from the median nerve MN, but also relative to the various tendons TN particularly upon the light source (not shown) being energized to create the light rays R (FIG. 10) illuminating the surgical area SA. After creating the surgical area SA and essentially isolating and illuminating the transverse carpal ligament TCL, the surgeon cuts the transverse carpal ligament TCL freeing or releasing the binding effect thereof and the pressure the latter exercised upon the tendons TN and the median nerve MN which subsequently relieves the typical carpal tunnel syndrome symptoms of pain, tingling, numbness, swelling, etc.

After the transverse carpal ligament TCL has been severed, the handle portions 13, 14 are released whereupon the spring 21 biases the blade portions 17, 18 from the open position (FIG. 10) to the closed position (FIG. 9). The instrument 10 is then rotated from the position shown in FIGS. 7 and 9 to the position shown in FIG. 6, withdrawn, and the incision I is closed or sutured.

With the above and other objects in view that will hereinafter appear, the nature of the invention will be more clearly understood by reference to the following detailed description, the appended claims and the several views illustrated in the accompanying drawings.

I claim:

1. A surgical instrument comprising a pair of legs, each leg including a handle portion disposed transverse to a blade portion, means uniting said handle portions for effecting movement of said blade portions between first and second positions in which said blade portions are in respectively adjacent and spaced relationship to each other, each blade portion being of a substantially elongated configuration converging along a longitudinal axis toward a terminal nose, each blade portion having a relatively broad inner face and a relatively broad opposite outer surface, said inner faces being in generally opposing adjacent relationship to each other in said first position and in generally opposing substantially spaced relationship to each other in said second position, and illuminating means disposed within an elongate slot extending along at least a substantial portion of the said broad inner face of the longitudinal extent of said one blade portion for emitting illumination generally in a transverse direction relative to said longitudinal axis from said broad inner face of one of said blade portions thereby to effectively illuminate a substantially large longitudinal area between said inner faces when said inner faces are in said second position.

2. The surgical instrument as defined in claim 1 wherein said illuminating means includes fiberoptic light means for illuminating the area between said blade portion faces.

3. The surgical instrument as defined in claim 1 wherein said illuminating means includes fiberoptic light means for illuminating the area between said blade portion faces, and said fiberoptic light means is at least in part housed within said one blade portion and extends transversely at least in part beyond said one blade portion inner face.

4. The surgical instrument as defined in claim 1 wherein said illuminating means includes fiberoptic light means for illuminating the area between said blade portion faces, and said fiberoptic light means is at least in part defined by a light ray emitter end housed within said one blade portion and a light conductor housed at least in part within the handle portion associated with said one blade portion.

5. The surgical instrument as defined in claim 1 wherein said illuminating means includes fiberoptic light means for illuminating the area between said blade portion faces, said fiberoptic light means is at least in part defined by a light ray emitter end housed within said one blade portion and a light conductor housed at least in part within the handle portion associated with said one blade portion, and said last-mentioned handle portion and one blade portion having first and second intersecting bores housing said respective light conductor and light ray emitter end.

6. The surgical instrument as defined in claim 1 wherein said illuminating means includes fiberoptic light means for illuminating the area between said blade portion faces, said fiberoptic light means is at least in part defined by a light ray emitter end housed within said one blade portion and a light conductor housed at least in part within the handle portion associated with said one blade portion, said last-mentioned handle portion and one blade portion having first and second intersecting bores housing said respective light conductor and light ray emitter end, and said second bore opens through said elongate slot of said one blade portion inner face.

7. The surgical instrument as defined in claim 1 wherein said one blade portion includes a generally cylindrical bore generally housing said illuminating means, and said cylindrical bore opens by way of said elongate elongated slot through said one blade portion inner face.

8. The surgical instrument as defined in claim 1 wherein said one blade portion includes a generally cylindrical bore generally housing said illuminating means, said cylindrical bore opens by way of said elongate elongated slot through said one blade portion inner face, and said cylindrical bore has a diameter greater than the width of said elongated slot.

9. The surgical instrument as defined in claim 1 wherein each blade portion has relatively narrow upper and lower surfaces.

10. The surgical instrument as defined in claim 9 wherein said one blade portion includes a generally cylindrical bore generally housing said illuminating means, said cylindrical bore opens by way of said elongated slot through said one blade portion inner face, said cylindrical bore has a diameter greater than the width of said elongated slot.

11. The surgical instrument as defined in claim 9 wherein said illuminating means includes fiberoptic light means for illuminating the area between said blade portion faces.

12. The surgical instrument as defined in claim 11 wherein said illuminating means includes fiberoptic light means for illuminating the area between said blade portion faces, and said fiberoptic light means is at least in part housed within said one blade portion.

* * * * *